United States Patent

Ashiya et al.

[11] Patent Number: 5,947,925
[45] Date of Patent: Sep. 7, 1999

[54] CATHETER ASSEMBLY

[75] Inventors: Hiroaki Ashiya, 25-1, Yoyogi 4-chome, Shibuya-ku, Tokyo; Junichi Fukamizu, Tokyo, both of Japan

[73] Assignees: Hiroaki Ashiya; Terumo Kabushiki Kaisha, both of Tokyo, Japan

[21] Appl. No.: 08/819,973

[22] Filed: Mar. 18, 1997

[30] Foreign Application Priority Data

Mar. 18, 1996 [JP] Japan .................................. 8-088910

[51] Int. Cl.⁶ .................................................. A61M 29/00
[52] U.S. Cl. .............................. 604/96; 604/95; 604/264; 604/523; 604/525
[58] Field of Search ................................ 604/95, 96, 265, 604/160, 161, 264, 200, 523, 525

[56] References Cited

U.S. PATENT DOCUMENTS

| | | |
|---|---|---|
| 4,762,129 | 8/1988 | Bonzel . |
| 4,876,126 | 10/1989 | Takemura et al. . |
| 4,988,356 | 1/1991 | Crittenden et al. . |
| 5,195,978 | 3/1993 | Schiffer . |
| 5,234,269 | 8/1993 | Grillo et al. . |
| 5,234,407 | 8/1993 | Teirstein et al. . |
| 5,364,376 | 11/1994 | Horzewski et al. . |
| 5,383,853 | 1/1995 | Jung et al. . |
| 5,389,087 | 2/1995 | Miraki . |
| 5,441,488 | 8/1995 | Shimura et al. . |
| 5,458,639 | 10/1995 | Tsukashima et al. . |
| 5,520,647 | 5/1996 | Solar . |
| 5,533,968 | 7/1996 | Muni et al. . |
| 5,549,551 | 8/1996 | Peacock, III et al. ................... 604/96 |
| 5,724,977 | 3/1998 | Yock et al. ...................... 128/662.06 |

FOREIGN PATENT DOCUMENTS

| | | |
|---|---|---|
| 0 397 357 | 11/1990 | European Pat. Off. . |
| 93/17750 | 9/1993 | WIPO . |
| 94/01164 | 1/1994 | WIPO . |
| 96/01604 | 1/1996 | WIPO . |
| 96/02295 | 2/1996 | WIPO . |

*Primary Examiner*—Wynn Wood Coggins
*Assistant Examiner*—N. Kent Gring
*Attorney, Agent, or Firm*—Burns, Doane, Swecker & Mathis, L.L.P.

[57] ABSTRACT

A highly safe catheter assembly exhibiting excellent torque transmission, pushability and kink resistance and operation of a guidewire is provided. The catheter assembly comprises a catheter having a lumen extending between an opening on its distal end and an opening in its periphery in distal end portion of the catheter for insertion of a guidewire therethrough, and a covering sheath for covering said catheter together with the guidewire, said covering sheath having a guidewire passage means for enabling passage of said guidewire from its interior to its exterior. The catheter of this assembly may be a PTCA catheter.

18 Claims, 10 Drawing Sheets

CATHETER ASSEMBLY

BACKGROUND OF THE INVENTION

This invention relates to a catheter assembly, and more specifically, to a catheter assembly which is used by inserting in a blood vessel.

Typical balloon catheters for insertion into a blood vessel such as catheters for PTCA (percutaneous transluminal coronary angioplasty) (hereinafter referred to as PTCA catheters) are provided with a lumen for guidewire passage formed along its full length in addition to the balloon inflating/deflating lumen. In the use of such catheters, the guidewire is preliminarily inserted in the guidewire passage lumen of the catheter before the catheter insertion into the blood vessel, and the catheter and the guidewire are simultaneously advanced within the blood vessel with the guidewire ahead of the catheter until their distal ends reach the target site, namely, around the stenosis in the blood vessel.

Figure 12:
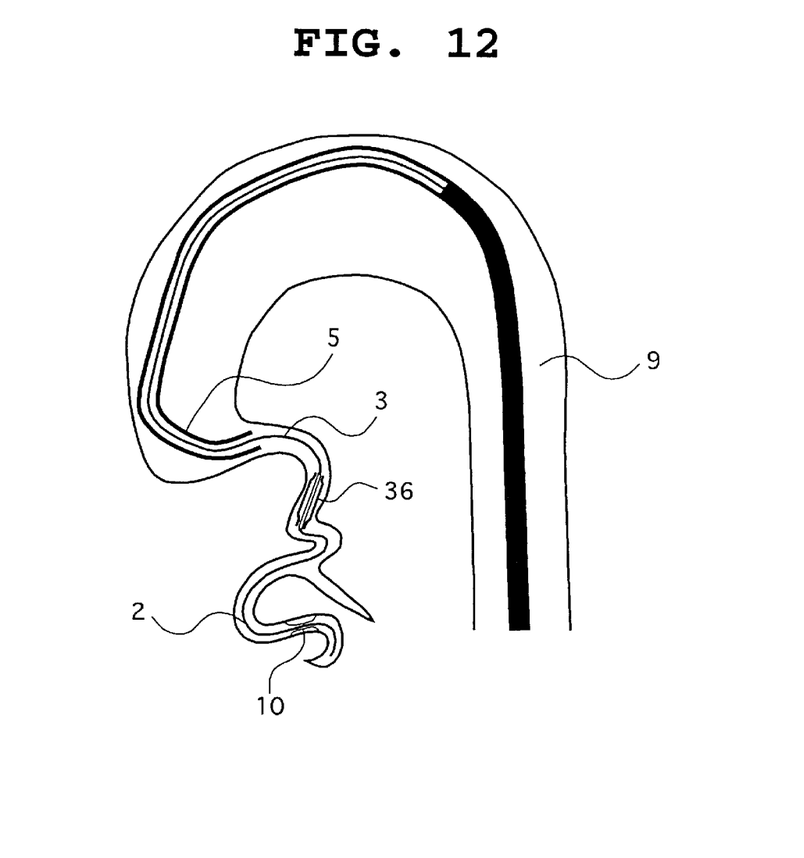
FIG. 12 is a schematic view of a body of a patient showing an operation of catheter.

This operation is very difficult, and a considerable skill was required to succesfully complete such operation. As shown in FIG. 12, in a typical process, a guiding catheter 5 accommodating a guidewire 2 and a catheter 3 is inserted into the blood vessel 9. Then the guiding catheter 5 is advanced in a blood vessel 9 until the distal end of the guiding catheter 5 reaches the entrance or a narrow blood vessel. The guidewire 2 and the catheter 3 provided with the balloon 36 are then advanced along the narrower blood vessel one after another until they reach near the stenosis lesion. The guidewire 2 is advanced to extend through and beyond the stenosis 10, and the catheter 3 is advanced along the guidewire 2 until the balloon 36 of the catheter 3 is positioned right within the stenosis 10. The balloon 36 is then inflated to dilate the stenosis 10. Such complicated operation must be conducted at the proximal extracorporeal end of the catheter by groping. Therefore, the structure, and hence, the operational convenience of the catheter and the guidewire are of great significance.

A wide variety of PTCA catheters are available for use in the cases of different stenosis sizes and blood vessel diameters, and PTCA catheters of different balloon sizes are also available for step-wise dilatation of the stenosis lesion. In some cases, exchange of the PTCA catheter that has been inserted in the blood vessel may become necessary. Repeated withdrawal and insertion of catheters is also carried out when a plurality of devices called stents are indwelled in the blood vessel for the purpose of maintaining the inner diameter of the blood vessel.

Preferably, such catheter exchange is effected with the guidewire being left in the blood vessel of the patient in order to reduce the burden of the patient, the time and trouble of the operation, and the risk of infection.

As described above, the lumen for guidewire passage in the conventional catheters extends along its full length. Therefore, for effecting catheter exchange by withdrawing the catheter out of the patient's body from the proximal end of the guidewire with the guidewire being retained in the patient's body, it has been necessary for the proximal extracorporeal end of the guidewire to extend beyond the proximal end of the catheter a length longer than the full length of the catheter. The extracorporeal end of the guidewire extending for such a long length has been quite an obstacle in the operation of the catheter.

In view of such situation, U.S. Pat. No. 4,762,129 proposes a catheter wherein the lumen for guidewire passage does not extend through its full length. The guidewire lumen of this patent catheter extends only between the distal end opening and an opening formed on the periphery of the catheter several centimeters proximal from the distal end, and the guidewire proximal of the guidewire lumen extends along the exterior of the catheter. The guidewire and the catheter are in engagement with each other only along the length of such short lumen, and therefore, this catheter can be exchanged while the guidewire is anchored in the patient's body, even if the guidewire protruded from the patient's body by a short length. Such catheter is known as a rapid exchange catheter.

When a catheter having a guidewire inserted through its guidewire lumen is advanced through the blood vessel of a patient to the target site, the guidewire and the catheter should be respectively handled on their extracorporeal ends (for example, on their femoral ends) by pushing and pulling the catheter/guidewire with occasional rotation, and such movement of the catheter/guidewire should be transmitted to their distal ends. Accordingly, the catheter should be provided with sufficient torque transmission and pushability. The catheter should also have a sufficient kink resistance to prevent the blockage of the balloon inflation lumen by folding of the catheter.

Figure 11:
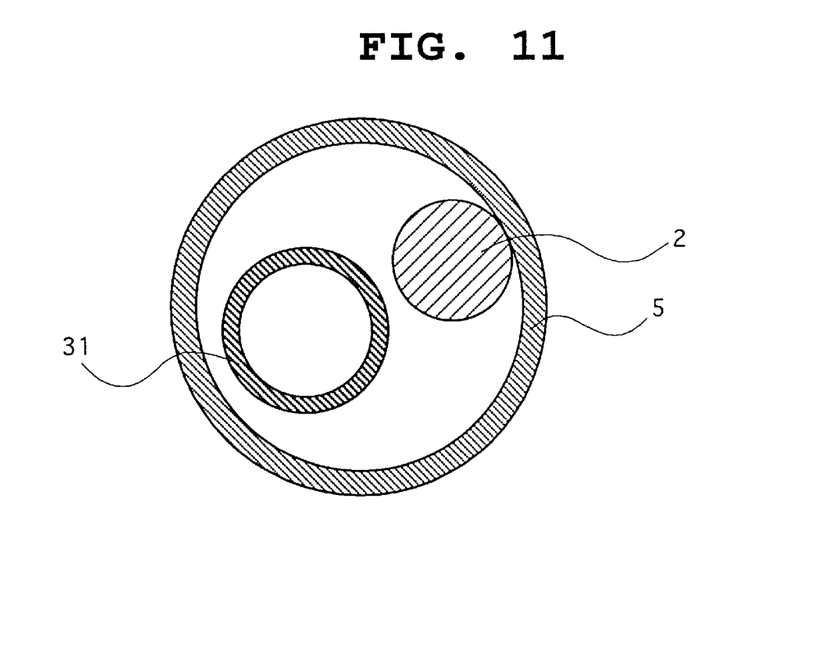
FIG. 11 is a transverse section of a conventional catheter.

However, in the rapid exchange catheter as described above, the rigidity (flexural rigidity and tortional rigidity) of the proximal portion of the catheter in the proximal side of said opening on the periphery (see FIG. 11), where the guidewire is not accommodated in the lumen, was significantly lower than the distal portion of the catheter in the distal side of said opening, where the guidewire is accommodated in the guidewire passage lumen. Due to such insufficiency in the rigidity of the proximal portion of the catheter, the catheter suffered from insufficient kink resistance, and insertion of such rapid exchange catheter into the blood vessel often proved unsuccessful.

Such catheter also suffered from insufficient torque transmission and pushability. One reason for such disadvantage was the play inevitably formed between the guiding catheter 5 and the catheter main segment (shaft) 31 since the guidewire 2 extended along the exterior of the catheter main segment 31 shown in FIG. 11. Another reason was the relatively small outer diameter of the catheter main segment, which was an inevitable consequence of separate accommodation of the guidewire 2 and the catheter main segment 31 within the interior of the guiding catheter 5.

SUMMARY OF THE INVENTION

An object of the present invention is to provide a catheter assembly which exhibits sufficient torque transmission, pushability, kink resistance and operation of a guidewire.

Another object of the present invention is to provide a catheter assembly which has enabled the exchange of the catheter with the guidewire retained in the blood vessel.

A further object of the present invention is to provide a catheter assembly wherein such exchange of the catheter can be readily effected.

Such objects of the present invention are realized by the present invention according to the following.

(1) A catheter assembly comprising a catheter having a lumen for insertion of a guidewire therethrough extending between a first opening on its distal end and a second opening in its periphery in distal end portion of the catheter, and a covering sheath for covering said catheter together with the guidewire, said covering sheath having a guidewire passage means for enabling passage of said guidewire from its interior to its exterior.

(2) A catheter assembly further comprising a guiding catheter for inserting said catheter and said covering sheath therethrough.

(3) A catheter assembly according to the above (1) or (2) wherein said guidewire passage means may be a slit or a thin-walled portion formed in said covering sheath to extend in longitudinal direction.

(4) A catheter assembly according to any one of the above (1) to (3) wherein said slit or thin-walled portion may be provided at its proximal end with a guide for guiding said guidewire into said slit or said thin-walled portion.

(5) A catheter assembly according to any one of the above (1) to (4) wherein a holder may be mounted on said covering sheath on one end thereof.

(6) A catheter assembly according to any one of the above (1) to (5) wherein said catheter may be provided in its periphery with a groove extending in longitudinal direction to hold said guidewire.

(7) A catheter assembly according to any one of the above (1) to (8) wherein said catheter may comprise a shaft and an inflatable/deflatable balloon provided on the distal end portion of the shaft.

(8) A catheter assembly according to the above (7) wherein said second opening may be in the proximal side on the periphery of the catheter from the proximal end of the balloon or in the distal side on the periphery of the catheter from the distal end of the balloon.

(9) A catheter assembly according to the above (7) wherein said balloon may be provided on one side of the catheter shaft, the second opening may be provided on the other side of the balloon.

(10) A catheter assembly according to the above (6) wherein said groove may extend between said second opening of said guidewire lumen on the periphery of said catheter and the proximal end of the catheter, and wherein said second opening may be covered by said covering sheath.

BRIEF DESCRIPTION OF THE INVENTION

PREFERRED EMBODIMENTS OF THE INVENTION

Next, the catheter assembly of the present invention is described in further detail by referring to the preferred embodiments shown in the attached drawings.

Figure 1:
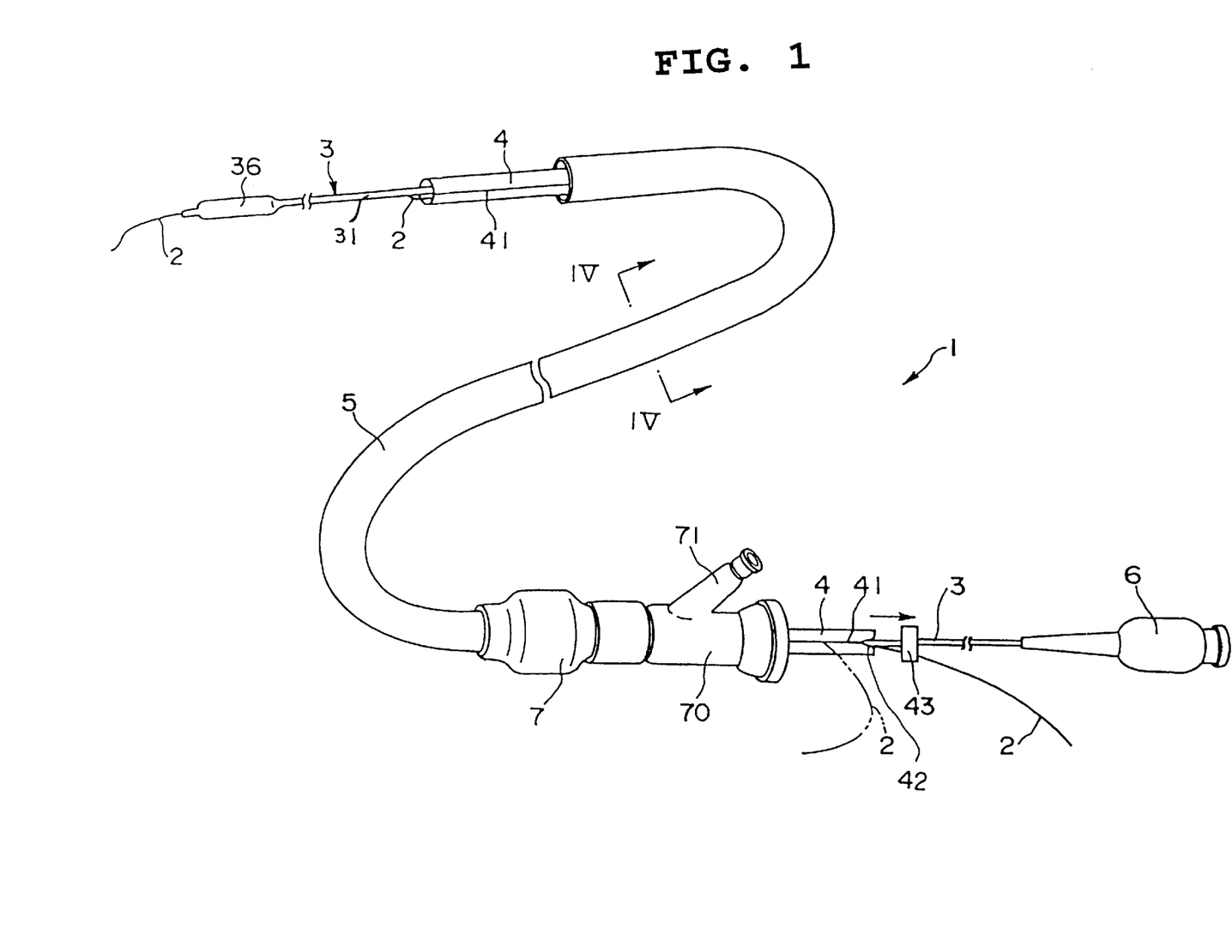
FIG. 1 is a perspective view of a catheter assembly according to one embodiment of the present invention.
Figure 2:
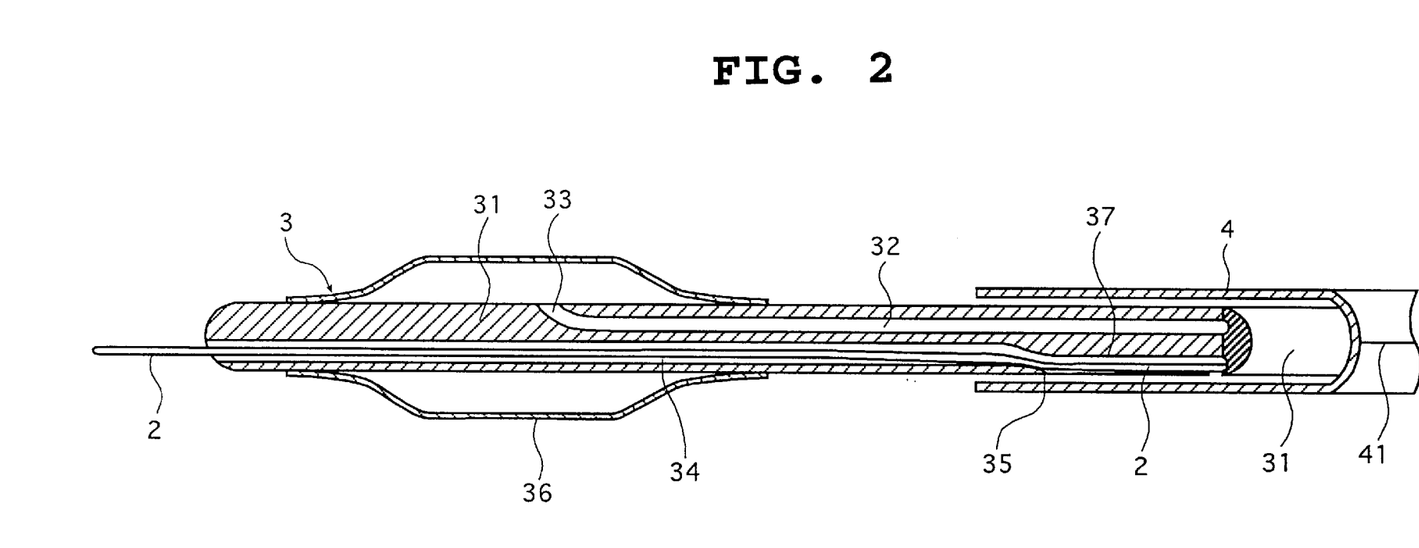
FIG. 2 is a partially cut-away longitudinal section of the catheter assembly of FIG. 1 showing the structure of its distal end portion.

FIG. 1 is a perspective view of a catheter assembly according to an embodiment of the present invention. FIG. 2 is a partially-cutaway longitudinal view of the catheter assembly of FIG. 1 showing the structure near it distal end.

FIG. 1 shows a catheter assembly 1 according to one embodiment of the present invention. The catheter assembly 1 comprises a guidewire 2; a catheter 3; a tubular covering sheath 4 for covering and reinforcing the catheter 3 and the guidewire 2; and a guiding catheter 5 through which the guidewire 2, the catheter 3 and the covering sheath 4 are inserted; a hub 6 provided on the proximal end of the catheter 3; and a hub 7 provided on the proximal end of the guiding catheter 5. The structure of these members are described below.

The guidewire 2 comprises a flexible wire. The material used for constituting the guidewire 2 is not limited to any particular material. Exemplary materials include metal materials such as super-elastic alloys, for example, a Ni—Ti alloy, stainless steel, piano wire and the like.

Preferably, the guidewire 2 is treated on at least a part of its surface to impart the surface with lubricity. The distal end of the guidewire 2 is tapered with the diameter of the guidewire 2 gradually decreasing toward its distal end to attain the desired properties, for example, butt resistance and flexural resistance. Smooth insertion of the guidewire 2 is thereby attained when the guidewire 2 is inserted in the blood vessel from its distal end and advanced therethrough to the target site such as coronary artery, since the distal end portion of the guidewire 2 can fully comply with the complicated configuration of the winding, branching blood vessels. Optionally withdrawal of the guidewire 2 is also facilitated. An easy, safe insertion of the guidewire 2 is thereby attained.

The guidewire 2 may have an outer diameter less than that of the catheter 3 and the guidewire 2 may have a largest possible outer diameter in view of the operational convenience.

The catheter 3 is a catheter of rapid exchange type preferably having a balloon. The catheter 3 comprises a shaft or flexible catheter main segment 31 and an inflatable/deflatable balloon 36 provided on the distal end portion of the catheter main segment 31 on its periphery.

The catheter main segment 31 may comprise a flexible polymer material. Exemplary materials include polyethylene, polypropylene, an ethylene-propylene copolymer, an ethylene-vinyl acetate copolymer, a crosslinked ethylene-vinyl acetate copolymer and other polyolefins, a polyester, polyvinyl chloride, a polyurethane, a polyamide, a polyimide, a polyamide elastomer, a polyurethane elastomer, a polyester elastomer, a polyfluororesin and other thermoplastic or thermoset resins, or a silicone rubber.

The catheter 3 may preferably have an outer diameter of from about 1.5 to 7.0 Fr (0.49–2.31 mm).

As shown in FIG. 2, the distal end portion of the catheter main segment 31 may preferably be formed with two lumens, namely, a first lumen 32 for balloon inflation/deflation and a second lumen 34 for the guidewire 2.

The first lumen (being called inflation lumen) 32 functions as a flow path in supplying an operational fluid for the inflation/deflation of the balloon 36 to the interior of the balloon 36. The first lumen 32 extends longitudinally within the catheter main segment 31 substantially along its full length except for the distal end portion of the catheter. The distal end of the first lumen 32 constitutes an opening 33 on the periphery of the catheter main segment 31 within the interior of the balloon 36. The first lumen 32 extends to the proximal end of the catheter main segment 31.

The second lumen (guidewire lumen) 34 for passage of the guidewire 2 is formed only in the distal end portion of the catheter main segment 31. The proximal portion of the lumen 34 is exposed to the exterior of the catheter main segment 31. Distal end of the second lumen 34 is a first opening 38 on the distal end of the catheter main segment 31. The proximal end of the second lumen 34 constitutes a second opening 35 on the periphery of the catheter main segment 31 preferably at a position proximal to the balloon 36.

Figure 7:
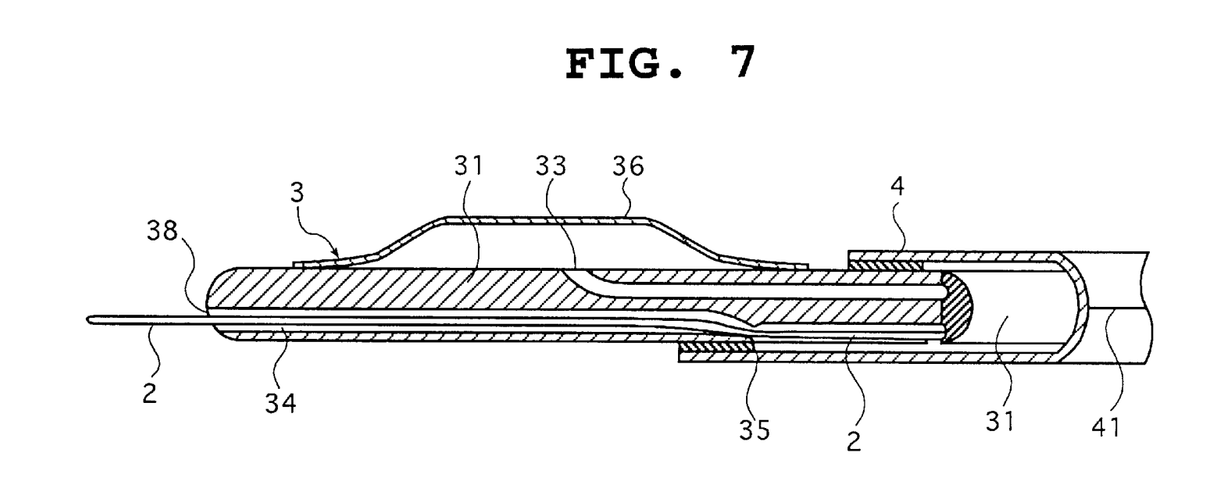
FIGS. 7 and 8 are partially cut-away longitudinal sections of catheter assemblies according to another embodiment of the present invention.

In the another embodiment of the present invention, as shown in FIG. 7, the balloon 36 may be provided on a part of the periphery of the catheter main segment 31 and the second opening 35 may be provided on the opposite side of the periphery of the catheter main segment 31 wherein the balloon is not provided.

Figure 8:
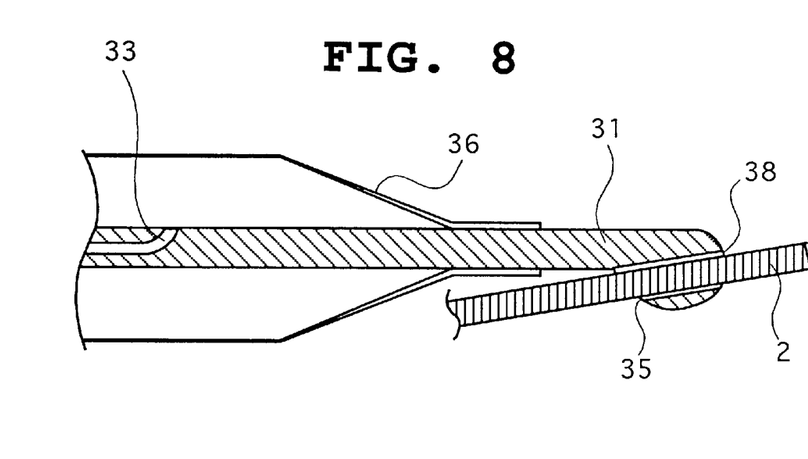

In the another embodiment of the present invention, as shown in FIG. 8, the first opening 38 and the second opening 35 may be in the distal portion of the catheter main segment 31, namely, the first opening 38 may be on the distal end of the catheter main segment 31, and the second opening 35 may be in the distal side from the distal end of the balloon 36.

The guidewire is inserted through the second lumen 34. The distal end of the guidewire 2 extends beyond the distal first opening 38 of the second lumen 34. The proximal end of the guidewire 2 extends beyond the second opening 35, being exposed to the exterior of the catheter main segment 31. The part of the guidewire 2 extending from the second opening 35 is disposed substantially parallel to the catheter main segment 31 along its periphery.

The diameter of the first lumen (inflation lumen) 32 is not limited to any particular range as long as the operational fluid for inflating/deflating the balloon 36 can be supplied/discharged through the lumen 32.

The length of the second lumen 34, namely the length from the first opening 38 to the second opening 35, is not limited to any particular range as long as the catheter can be smoothly exchanged. The second lumen 34, however, may preferably have a length in the range of from about 1.5 to 130 cm, and more preferably, from about 2.5 to 30 cm.

The diameter of the second lumen 34 is not limited to any particular range as long as the guidewire 2 can be smoothly inserted therethrough.

In the periphery of the catheter main segment 31 is preferably formed a groove or recess 37 extending in the longitudinal direction of the catheter 3. The distal end of the groove 37 is connected to the second opening 35, and the groove 37 extends to the proximal end of the covering sheath 4 or to the vicinity of the proximal end of the covering sheath 4.

Figure 4:
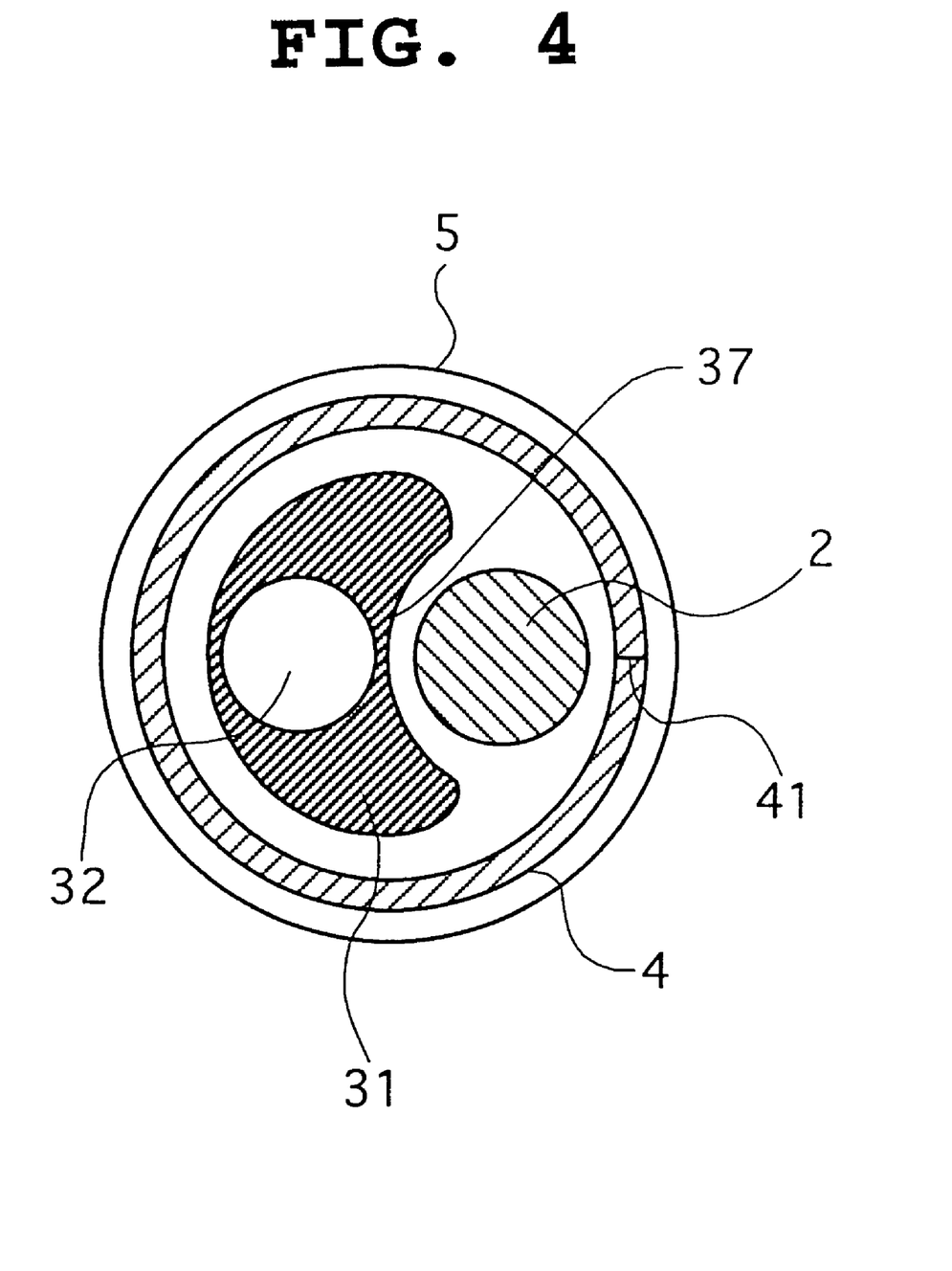
FIG. 4 is a transverse section of the catheter assembly of FIG. 1 taken along lines IV—IV.
Figure 5:
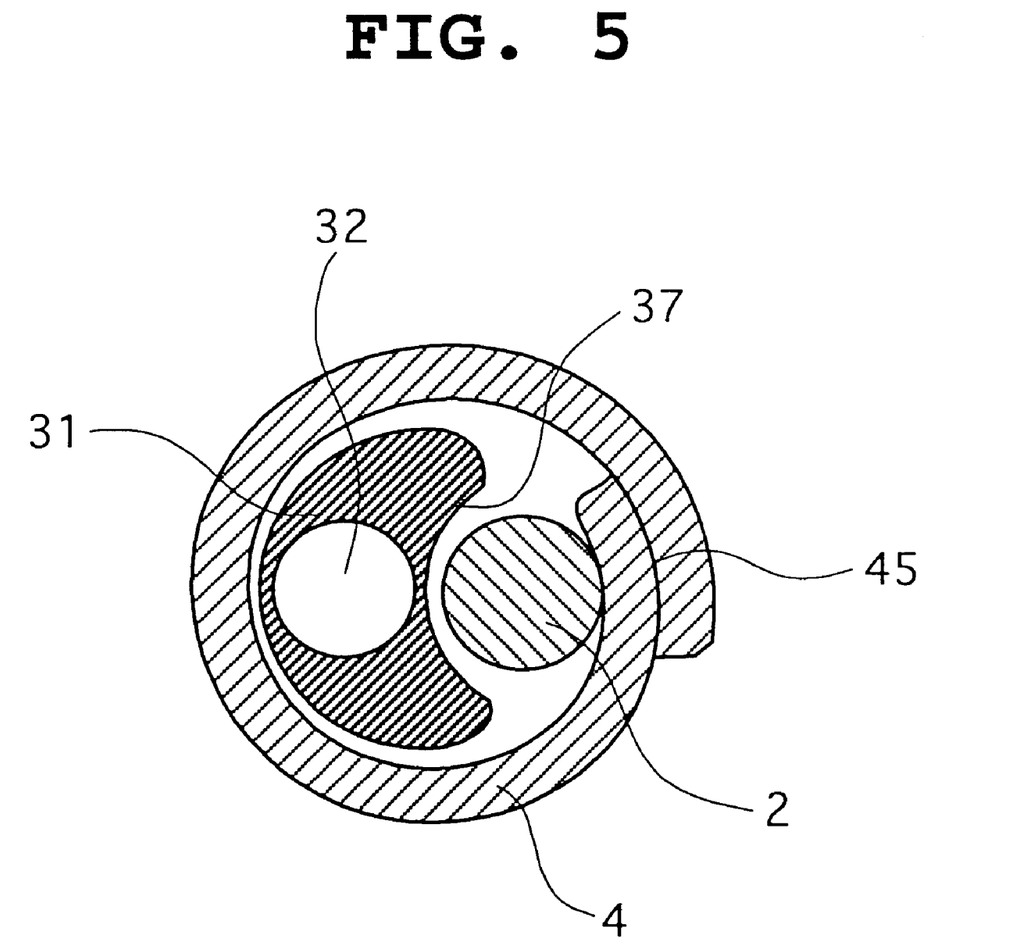
FIGS. 5 and 6 are transverse sections of the catheter assemblies according to another embodiments of the present invention.
Figure 6:
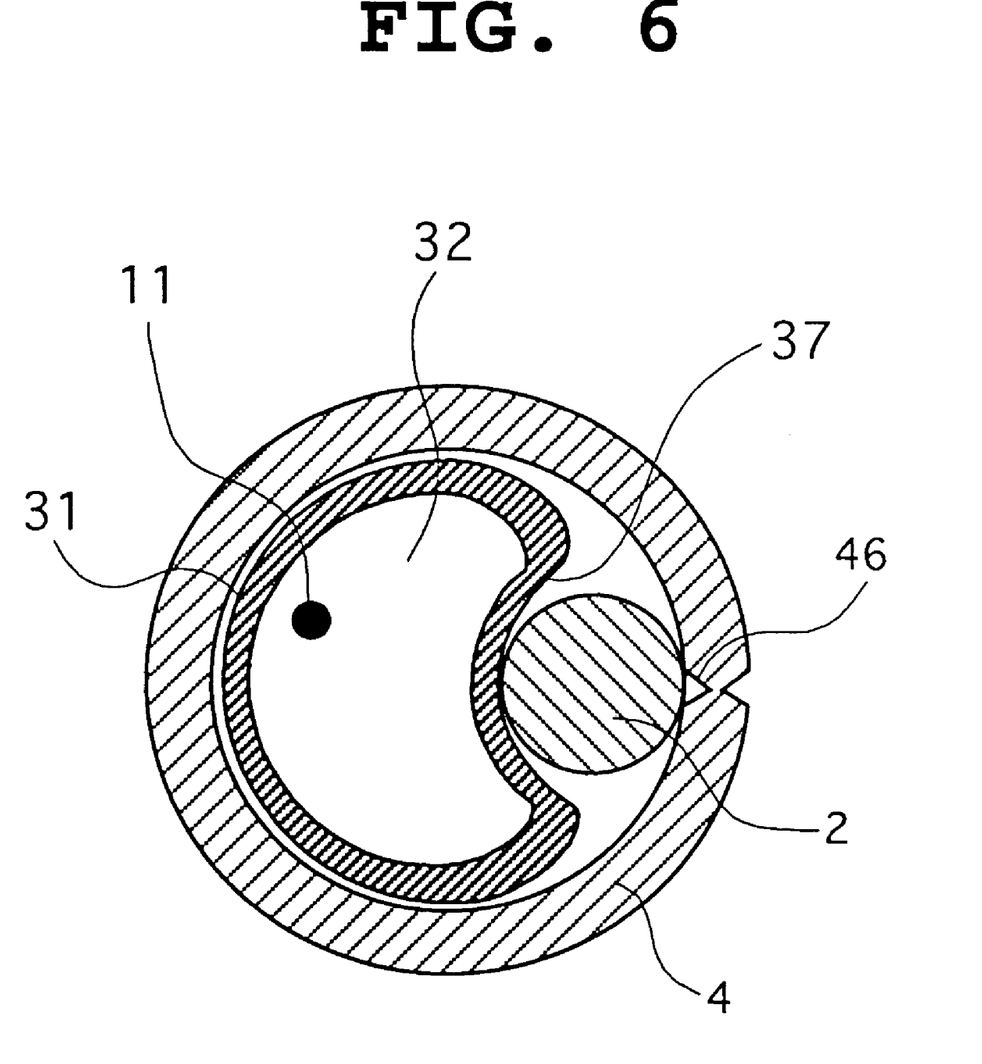

The groove 37 may have any cross section as long as it is capable of fully or partially holding the guidewire 2, and in the present embodiment, the groove 37 has a substantially semicircular cross section, and the catheter main body has a substantially crescent cross section as shown in FIGS. 4 to 6.

Provision of the groove 37 along the catheter main segment 31 has the advantages as described below. When the catheter main segment 31 is subsequently covered with a covering sheath 4, preferably in a tight manner without adversely effect the operation of the guidewire as described below, the guidewire 2 accommodated within the groove 37 will be fixedly secured to the catheter 3, and no play will be left around the guidewire 2, allowing no lateral movement of the guidewire 2 in relation to the catheter main segment 31. Upon manipulation of the catheter main segment 31, the guidewire 2 would then be deformed simultaneously with the catheter main segment 31, resulting in surprisingly improved torque transmission, pushability, and kink resistance of the catheter main segment 31.

The groove 37 also functions as a guideway for the catheter 3 in a way that the catheter 3 may be advanced and retracted along the guidewire 2 included in its groove 37.

The balloon 36 comprises a film tubular member, and opposite ends of the balloon 36 are fixedly secured to the periphery of the catheter main segment 31 by adhesion or heat sealing in an air-tight and liquid tight manner.

The balloon 36 may be formed from a material with a certain flexibility. Exemplary materials include polyethylene, polypropylene, an ethylene-propylene copolymer, an ethylene-vinyl acetate copolymer, a crosslinked ethylene-vinyl acetate copolymer and other polyolefins such as a crosslinked polyolefin, a polyester, polyethylene terephthalate, polyvinyl chloride, a polyurethane, a polyamide, polyamide elastomers and other thermoplastic or thermoset resins, silicone rubbers, and latex rubbers.

In addition to the structural components as described above, the catheter may comprise further lumens and further reinforcements as desired, which may fully or partly extend along the catheter.

The catheter 3 and the guidewire 2 as described above are covered with the covering sheath 4 at least in the part proximal to the second opening 35. The covering sheath 4 is a substantially tubular member with a substantially circular, namely, C-shaped cross section as shown in FIG. 4. The covering sheath 4 is preferably in tight contact with the catheter main segment 31 and the guidewire 2 to an extent that the movement of the guidewire 2 is not hindered. The covering sheath 4, therefore, reinforces the catheter 3 and guidewire 2.

The covering sheath 4 is formed from a flexible material provided with an appropriate rigidity (flexural rigidity and tortional rigidity) and an appropriate breaking strength. The covering sheath 4 may preferably comprise a film of polymer (synthetic resin) material as listed below.

The covering sheath 4 may comprise a film material prepared from such materials as polyolefins such as polyethylene, polypropylene, an ethylene-propylene copolymer, an ethylene-vinyl acetate copolymer and a crosslinked ethylene-vinyl acetate copolymer; polyesters such as polyethylene terephthalate and polybutyrene terephthalate; polyvinyl chloride, polystyrene, a polyurethane, a polyamide, a polyimide, a polyamideimide, a polycarbonate, acrylic resin, an ABS resin, polymethylmethacrylate, a polyacetal, a polyallylate, polyoxymethylene, polyvinylalcohol, polytetrafluoroethylene, polyfluorovinylidene and other fluororesins, polysulfone, polyethersulfone, polyphenylenesulfide, polyetherketone, a liquid crystaline polymer, and a copolymer, a polymer blend and a polymer alloy based on such resins, and a combination of two or more of the above-mentioned resins, for example, in the form of a laminate of two or more layers.

The thickness of the film constituting the covering sheath 4 is not limited to any particular range. The covering sheath 4 should then have sufficient flexibility and rigidity, and hence, satisfactorily improved torque transmission, pushability, and kink resistance. The film, however, may preferably have a thickness of about 5 to 800 $\mu$m.

If the catheter main segment 31 is constituted from a soft material, the covering sheath 4 may be made from a rather rigid material. The covering sheath 4 having the catheter main segment 31 and the guidewire 2 accommodated therein should then have satisfactorily improved torque transmission, pushability, and kink resistance.

The covering sheath 4 may preferably have a length equal to or shorter than the length of the catheter having the length of the balloon subtracted therefrom. The covering sheath 4 may generally have a length of from about 80 to 130 cm.

The covering sheath 4 as described above is provided with a guidewire passage means 45 for passing or moving the guidewire from the interior to the exterior of the covering sheath 4. In one embodiment, the guidewire passage means is formed along the covering sheath 4 in its longitudinal direction as a slit or a thin-walled portion along which the side wall of the covering sheath 4 is separable. The constitution of the guidewire passage means is more precisely described in the following.

Figure 3:
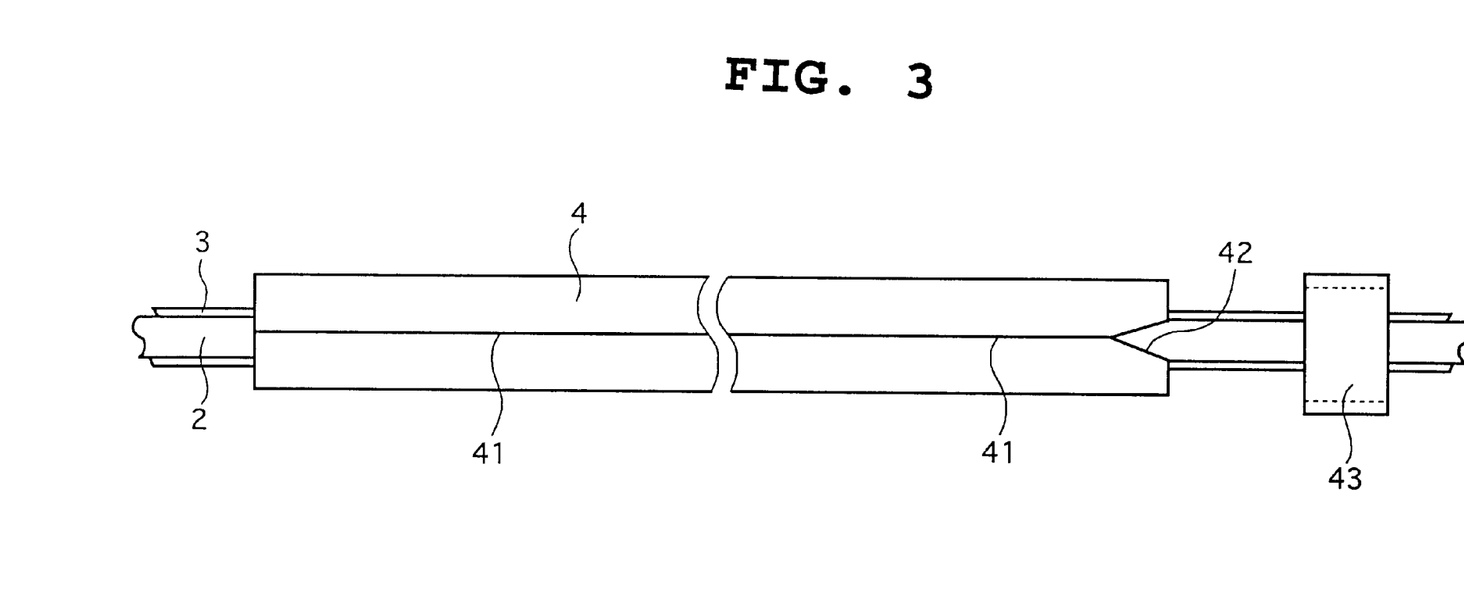
FIG. 3 is a side view of the catheter assembly showing the covering sheath according to one embodiment of the present invention.

FIG. 3 is a side view of an embodiment of the covering sheath 4 assembled with the guidewire 2 and the catheter 3. In this embodiment of FIG. 3, the covering sheath 4 is formed with a slit 41 formed therealong in its longitudinal direction, and the wall of the covering sheath 4 is separable along the slit 41. In this embodiment, the opposite faces of the slit 41 lightly or forcedly abuts at the slit 41 without being adhered to each other. The opposite faces of the slit 41, however, may be weekly adhered to each other by an adhesive either partly or along its full length to a degree breakable and separable upon passage of the guidewire 2.

The slit 41 is provided at its proximal end with a guiding means in the form of a V-shaped notch 42 so that the guidewire 2 may be guided into the slit 41. It should be noted that the shape of the notch 42 is not limited to the shape shown in FIG. 3, and instead, the notch 42 may be formed only in one side along to the slit 4.

The guiding member may not necessarily be in the form of a notch, and the proximal end of the covering sheath 4 may be appropriately folded to form a space similar to the notch.

A ring-shaped holder 43 may be fitted around the proximal end of the covering sheath 4. The holder 43 prevents the proximal end portion of the covering sheath 4 from being loosely opened during insertion of the catheter 3 into the blood vessel. When the catheter 3 is exchanged with another catheter with the guidewire 2 retained in the blood vessel, the holder 43 is removed from the covering sheath 4 as shown in FIG. 1.

The holder 43 may not necessarily be in the form of a ring as shown in the drawings as long as it prevents the proximal end portion of the covering sheath 4 from being loosely separated. The holder 43 may be in the form of a holding member such as a clip, a peelable or cleavable adhesive tape, an adhesive, or the like. The holder 43 may be provided at other positions of the covering sheath 4, for example, at distal end of the covering sheath 4.

FIG. 4 is a cross-sectional view of taken along lines IV—IV of FIG. 3.

FIGS. 5 and 6 are cross sections showing other embodiments of the covering sheath 4 respectively showing the guidewire passage means of different structures.

The covering sheath 4 shown in FIG. 5 has a C-shaped cross section. This member is curled by the contraction force in the direction to reduce the diameter, and a consequence, longitudinal edges of the covering sheath 4 overlaps with each other to form the guidewire passage means 45.

In this embodiment, the opposite faces of the guidewire passage means 45 lightly or forcedly contact along the means 45 without being adhered to each other. The opposite faces of the means 45, however, may be weekly adhered to each other either partly or along its full length to a degree breakable and separable upon passage of the guidewire 2.

The covering sheath 4 shown in FIG. 6 has a circular cross section, and a thin-walled portion 46 of a guidewire passage means extending in longitudinal direction is defined at one section thereof by forming mutually facing longitudinal grooves on the interior and exterior surfaces of the covering sheath 4. The thin walled portion 46 may be defined by forming a longitudinal groove of either V-shaped or U-shaped cross section on either or both of the interior and exterior surfaces of the covering sheath 4.

The thin-walled portion 46 may comprise a material different from the covering sheath 4.

The thin-walled portion 46 may be adjusted to have a strength just breakable and separable by the tension of the guidewire 2 that has been guided into the notch 42, or by the deformation of the covering sheath 4 by the force applied from the proximal end.

The covering sheath 4 having such thin-walled portion 46 has a higher strength and rigidity since no slit is formed in the periphery. Therefore, design parameters such as the material used, thickness, and the like of wider choice may be adopted. The covering sheath 4 having such a thin-walled portion 46 is also convenient to use since care must be taken only when the thin-walled portion 46 has been broken and the guidewire 2 is being passed therethrough.

The covering sheath 4 may have an interior diameter that facilitates the tight contact of the covering sheath 4 with the catheter main segment 31 and the guidewire 2 while enabling smooth axial and rotational movement of the catheter main segment 31 and the guidewire 2.

In the catheter assembly 1 of the present invention, the exterior surfaces of the covering sheath 4 and the catheter 3 may preferably be formed with a layer (not shown) of a hydrophilic polymer material which exhibits lubricity in wet conditions. Such hydrophilic layers may reduce the friction in the insertion of the catheter 3 with the covering sheath 4. Smooth insertion as well as improved handling convenience and safety are thereby attained.

Exemplary hydrophilic polymer materials include natural polymer base resin such as those based on starch, cellulose, polysaccharide, and the like; and synthetic polymer base resin such as those based on PVA, polyethylene oxide, acrylic acid, maleic anhydride, phthalic acid, water-soluble polyester, (meth)acrylamide, polyamine, water-soluble nylon, and the like.

Among these, the preferred are cellulose-based polymers such as hydroxypropylcellulose; polyethylene oxide-based polymers such as polyethylene glycol; maleic anhydride-based polymers such as maleic anhydride copolymer, for example, methylvinylether-maleic anhydride copolymer; acrylamide polymers such as polydimethyacrylamide; water-soluble nylons such as AQ-Nylon P-70 manufactured by Toray K.K., and derivatives thereof in view of stably attained low frictional coefficient. Further details are described for example, in U.S. Pat. No. 4,876,126 and U.S. Pat. No. 5,441,488 which are herein incorporated by reference.

As shown in FIG. 1, the proximal end of the catheter 3 extends beyond the proximal end of the covering sheath 4, and a hub 6 is mounted on the proximal end of the catheter 3. The interior lumen of the hub 6 is connected to the proximal end of the first lumen 32 formed in the catheter main segment 31, and the operational fluid is supplied and withdrawn into and from the first lumen 32 from the hub 6 to thereby inflate and deflate the balloon 36.

The guidewire 2, the catheter 3 and the covering sheath 4 as described above are used after inserting such members in the guiding catheter 5.

The guiding catheter 5 is a flexible tubular member having an inner diameter larger than the outer diameter of the covering sheath 4. The guiding catheter 5 comprises a material suitably selected from the materials described in relation to the catheter main segment 31.

The outer diameter of the guiding catheter 5 is preferably less than the inner diameter of the coronary artery, and therefore, up to 10 Fr (3.33 mm).

The guiding catheter 5 is formed from a material having a radiopaque material incorporated therein, and therefore, the location of the distal end of the guiding catheter 5 may be easily confirmed with the aid of X ray, and operational convenience and safety are greatly improved.

As shown in FIG. 1, the guiding catheter 5 is connected in its proximal end with a hub 7, and the hub 7 is connected to a Y connector 70. The hub 7 and the Y connector 70 are both provided with a lumen, which are in communication with the lumen of the guiding catheter 5. The guidewire 2, the catheter 3 and the covering sheath 4 extend through the lumens of the guiding catheter 5, the hub 7, and the Y connector 70, and extend beyond the proximal end of the Y connector 70.

The Y connector is provided with a tubular branch 71. The branch 71 is used, for example, in injecting a contrast medium in the blood vessel of the target site. The contrast medium injected through the branch 71 advances through the lumens of the connector 70 and the guiding catheter 5 to be injected from the opening at distal end of the guiding catheter 5.

The guidewire, the catheter or the guiding catheter of the present invention may be preliminarily bent at a particular position to comply with the particular anatomy of the blood vessel. In addition, the catheter of the present invention may have a biased cross section or made from a super elastic alloy to facilitate curvature of the catheter at a particular direction.

Figure 9:
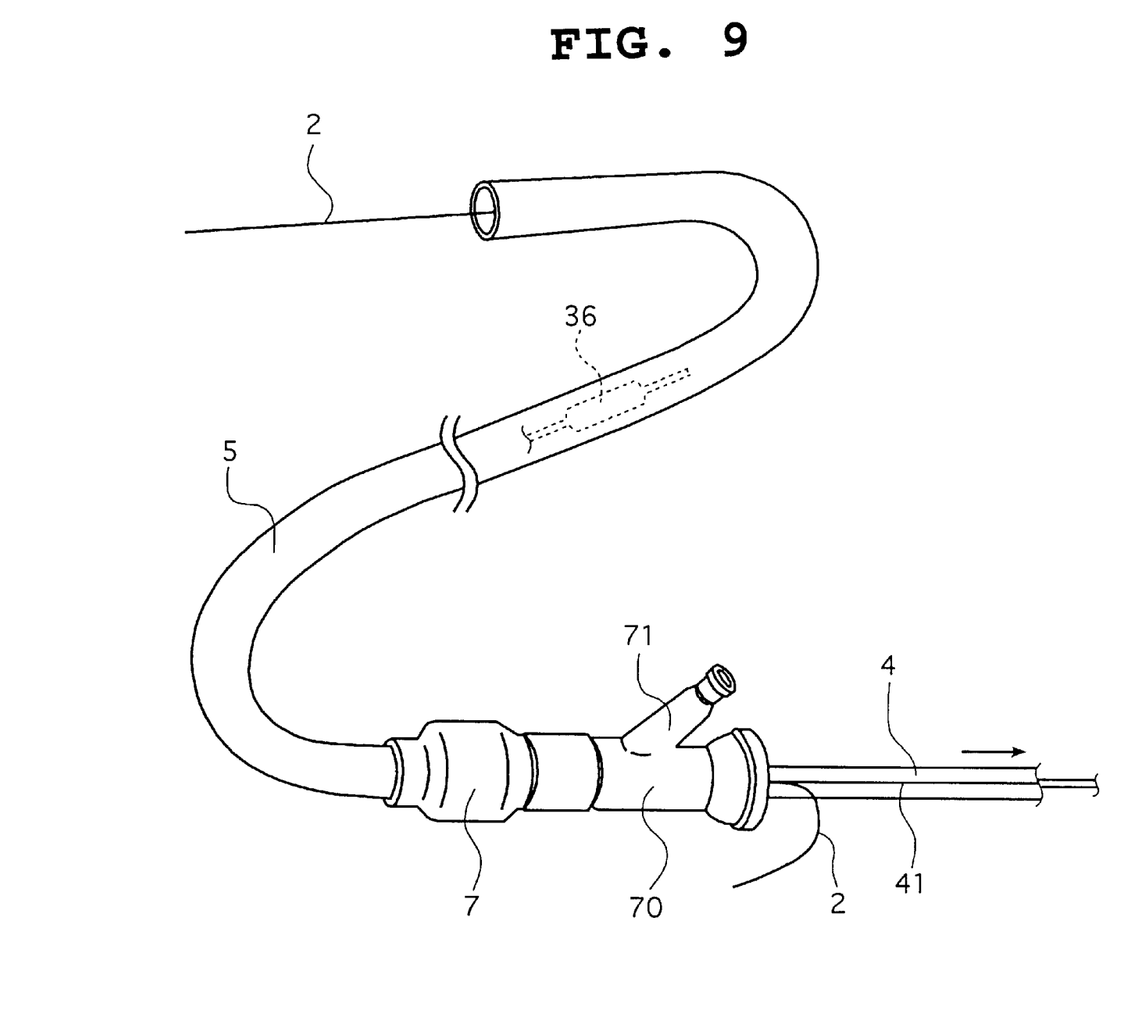
FIGS. 9 and 10 are perspective views of the catheter assembly of FIG. 1 wherein catheter exchange procedure is schematically shown.
Figure 10:
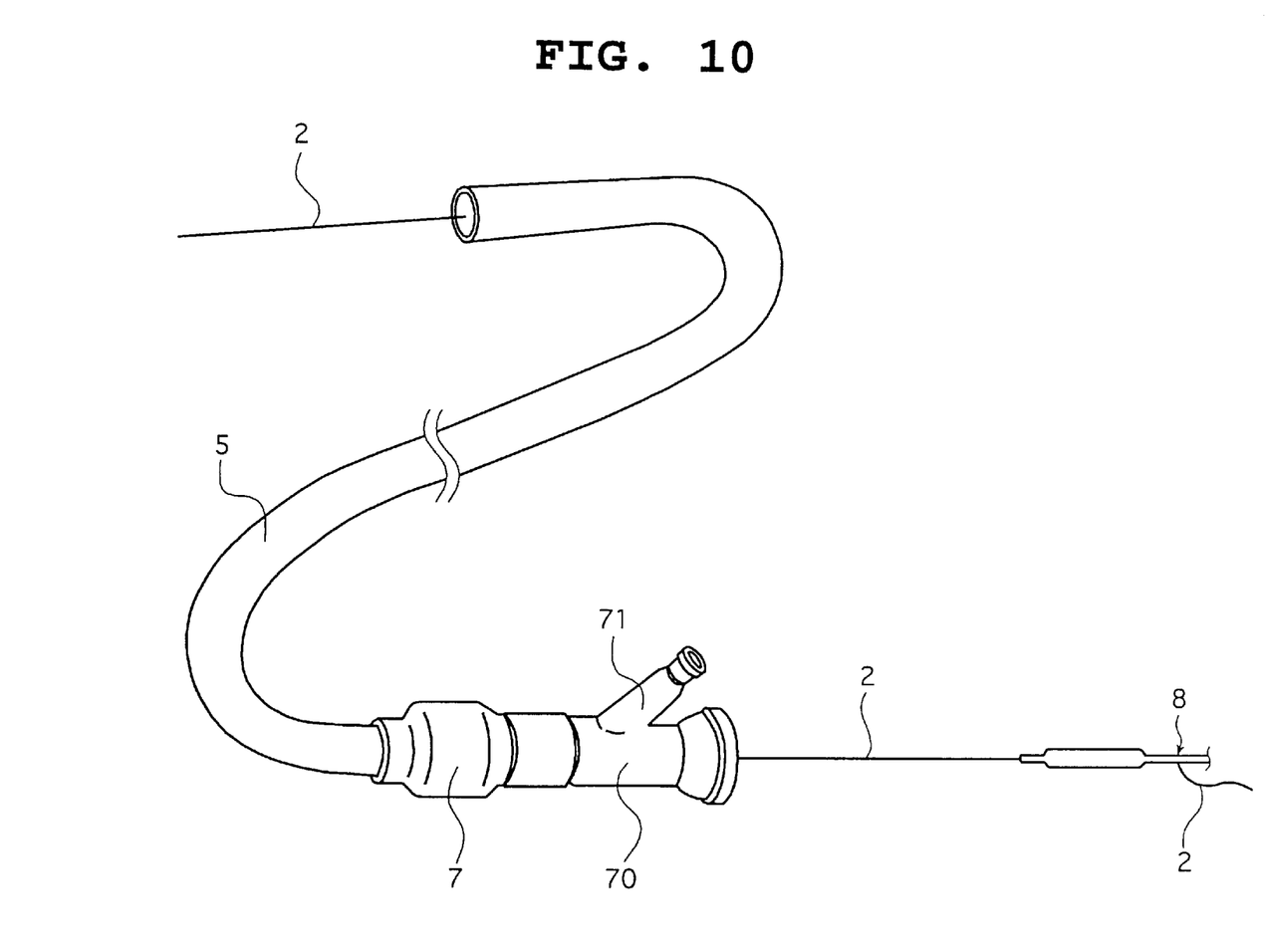

Next, method for using the catheter assembly 1 of the present invention in PTCA is described by referring to FIGS. 1, 9 and 10.

A catheter introducer is placed in femoral artery or brachial artery. The guiding catheter 5 having a guidewire (not shown) and a catheter covered with the covering sheath 4 inserted therethrough is guided into the artery from the sheath of the catheter introducer, and passed through the artery until its distal end reaches the inlet of the coronary artery where it is retained. During the passage of the guiding catheter 5 through the artery, the guiding catheter 5 and the guidewire 2 are repeatedly pushed forth and pulled back one after another with occational rotational movement.

In the catheter assembly of the present invention, the guidewire 2 extends from the first opening 38 to the second opening 35, and further, along the space defined by the groove 37 and the interior of the covering sheath 4. The guidewire 2 in the proximal side of the second opening 35 and the catheter main segment 31 in the proximal side of the balloon are covered by the covering sheath 4.

When the distal end of the guiding catheter 5 has been retained at the entrance of the coronary artery, the guidewire 2 is advanced and retracted with occasional rotation along the tortuous blood vessel toward the stenosis lesion. The catheter 3 is also advanced through the lumen of the guiding catheter 5 with occasional rotational movement until the distal end of the catheter 3 extends beyond the distal opening of the guiding catheter 5. It should be noted that, when the catheter 3 is advanced though the lumen of the guiding catheter, the covering sheath 4 also advances with the catheter 3.

When the catheter 3 covered with the covering sheath 4 is inserted as described above, the catheter 3 exhibits improved torque transmission and pushability upon rotation and advancement of the catheter 3 since the covering sheath 4 reinforces the part of the catheter 3 wherein the guidewire 2 is not embedded in the lumen (the portion of the catheter 3 in the proximal side of the second opening 35). Therefore, the handling convenience of the catheter is greatly improved, and the catheter can be readily and reliably inserted with high safety. The reinforcement of the catheter main segment 31 by the covering sheath 4 also results in an improved kink resistance of the catheter 3, and the blockage of the first lumen 32 or the like by the folding of the catheter main segment 31 is thereby prevented.

Once the distal end of the catheter 3 has reached into the coronary artery, the guidewire 2 is advanced therethrough with occasional rotation until its distal end passes through the coronary artery stenosis lesion, which is the target site. In the present invention, the catheter 3 is provided with the covering sheath 4, and therefore, upon rotation of the catheter 3, the guidewire 2 is rotated simultaneously with the catheter 3. Twining of the guidewire 2 around the catheter 3 is thereby prevented, and smooth handling of the guidewire 2 is thereby attained. Consequently, the passage of the guidewire 2 through the coronary artery stenosis lesion may be readily effected with a high reliability.

In the meanwhile, an X-ray contrast medium is injected from the branch 71 of the Y connector 70, and supplied to the coronary artery through the lumens of the Y connector 70, hub 7 and the guiding catheter 5, and X-ray irradiation for confirmation purpose is conducted.

When the distal end of the guidewire 2 has passed the coronary artery stenosis lesion, advancement of the guidewire 2 is terminated. The catheter 3 is then slowly advanced along the guidewire 2 to place the balloon 36 in the coronary artery stenosis lesion.

Next, an operational fluid such as an X-ray contrast medium is injected from the hub 6 and fed to the balloon 36 through the lumen of the hub 6 and the first lumen 32 to inflate the balloon 36 (see FIG. 1), and to thereby dilate the stenosis of the coronary artery.

To effect further dilatation of the coronary artery stenosis, the catheter must be replaced with the one equipped with a larger balloon.

In order to replace the catheter 3 that has been inserted into the coronary artery with a new catheter, the balloon 36 is first deflated and the hub 6 is pulled in proximal direction to withdraw the catheter 3 from the blood vessel while retaining the guidewire 2 and the guiding catheter 5 in their position without moving. Before this operation, the holder 43 is removed from the proximal end of the covering sheath 4; the guidewire 2 is withdrawn from the holder 43; and the guidewire 2 is guided into the slit 41 from the notch 42 as shown by the dash/dot/dot line in FIG. 1, with the proximal side of the guidewire 2 being held by fingers or the like. The catheter 3, therefore, can be withdrawn from the patient's blood vessel while the guidewire 2 is retained in the patient's body.

In FIG. 9, there is shown the guidewire 2 that has been introduced into the slit 41 near the proximal end of the hub 9. When the catheter 3 is withdrawn from the guiding catheter 5, the covering sheath 4 is also withdrawn together with the catheter 3. Upon withdrawal of the catheter 3 and the covering sheath 4, the guidewire 2 that has been introduced into the slit 41 advances along the slit 41 in distal direction in relation to the covering sheath 4. In other words, the guidewire 2 that had been located within the interior of the covering sheath 4 gradually passes through the slit 41 to be located in the exterior of the covering sheath 4.

When the thin-walled portion 46 as described above is employed instead of the slit 41, the covering sheath 4 may be deformed beforehand to break the thin-walled portion 46 for passage of the guidewire 2, or alternatively, the catheter 3 and the covering sheath 4 may be withdrawn simultaneously with the breakage of the thin-walled portion 46 by the tension of the guidewire 2.

When the distal end of the covering sheath 4 is withdrawn from the proximal opening of the hub 7 and the guidewire 2 has been fully moved to the exterior of the covering sheath 4, the catheter 3 is further withdrawn from the proximal opening of the hub 7 until the guidewire is fully removed from the second lumen 34 of the catheter 3 as shown in FIG. 10. The guidewire 2 would then be the only member remaining in the guiding catheter 5.

Next, as shown in FIG. 10, the proximal end of the guidewire 2 is inserted into the distal opening of the replacement new catheter 8 which is typically a balloon catheter. The new catheter 8 has also a guidewire lumen at its distal end, if the new catheter 8 is also rapid exchange type catheter. The new catheter 8 is inserted in the guiding catheter 5 along the guidewire 2 by its guidewire lumen, and advanced along the guidewire 2 and through the lumens of the Y connector 70, the hub 7, and the guiding catheter 5 until the catheter 8 reaches the target site. The replacement of the catheter is thus completed. The manipulation corresponding to the purpose of the particular replaced catheter 8 is then conducted. It should be noted that the new catheter replaced may be either a conventional catheter or a catheter assembled with a covering sheath according to the present invention. When the new catheter replaced is the one assembled with the covering sheath according to the present invention, the proximal end of the guidewire is inserted through the second lumen from the distal first opening to the second opening of the catheter, and the guidewire is laid along the catheter in the proximal side of the second opening. The covering sheath is covered over the guidewire. The guidewire and the catheter are then inserted in the guiding catheter.

The catheter assembly of the present invention has been explained according to the embodiments shown in the drawings. The present invention, however, is by no means limited to such embodiments.

For example, the catheter 3 may be of the type free from the balloon 36 and the first lumen 32. Alternatively, the catheter 3 may be of the type provided with additional one or more lumens, for example, a liquid injection lumen (flash lumen), which is adapted for introduction of a liquid such as a contrast medium or a pharmaceutical agent. The catheter 3 may be of the type wherein a reinforcement wire 11 in FIG. 6 is provided within the inflation lumen.

The catheter assembly of the present invention is not only adapted for use with a PTCA (percutaneous transluminal coronary angioplasty) catheter but also for the purpose of inserting and transporting a stent, and with an endoscope.

EFFECTS OF THE INVENTION

As described above, when the catheter assembly of the present invention is used and the catheter is replaced with a new catheter while the guidewire is left in the body of the patient, the catheter replacement may be readily effected by a simple procedure, and in particular, by one operator, since the lumen for the passage of the guidewire is formed only in the vicinity of the distal portion of the catheter.

In spite of such structure, the operativity of the catheter is not at all sacrificed. The catheter of the present invention is formed with a groove or recess which extends along the periphery of the catheter to hold the guidewire, and the proximal opening of the guidewire lumen on the periphery of the catheter and the groove having held the guidewire thereby are covered with a covering sheath. Therefore, the catheter has sufficient torque transmission, pushability, and kink resistance, and both the catheter and the guidewire are provided with improved handling convenience.

The covering sheath is formed with the guidewire passage means to enable the passage of the guidewire from the interior to the exterior of the covering sheath. Therefore, the catheter may be reliably exchanged while the guidewire is retained in the patient body.

As summarized above, the catheter assembly provided by the present invention is highly safe, and insertion and exchange of the catheter can be effected with ease.

Such advantages are particularly noticeable when the guidewire passage means is a slit or a thin-walled portion in the covering sheath formed along its longitudinal axis, in spite of the simple structure.

When the slit or the thin-walled portion is provided on its proximal end with a guide for guiding the guidewire, the guidewire may be smoothly guided into the slit or the thin-walled portion.

When the holder is detachably mounted on the proximal end of the covering sheath, separation or loosening of the proximal end of the covering sheath during insertion or the like of the catheter is prevented.

When the catheter used in the catheter assembly is a balloon catheter, a PTCA catheter may be used for the balloon catheter, and the catheter assembly can be used in the PTCA. Handling capability of the catheter during the insertion and the exchange of the catheter in PTCA is greatly improved.

I claim:

1. A catheter assembly comprising:
   a catheter which comprises:
   a shaft comprised of flexible polymer material, said shaft having a distal end and a proximal end, said shaft possessing a periphery, and
   an inflatable/deflatable balloon provided on the distal end portion of the shaft, said inflatable/deflatable balloon having a distal end and a proximal end;
   a covering sheath for covering said catheter together with a guidewire, said covering sheath comprising a synthetic resin material, said covering sheath having a distal end and a proximal end;
   said catheter having a lumen extending in said catheter for insertion of the guidewire therethrough, said lumen having a first opening on the distal end of the shaft and a second opening on the periphery of the shaft at a location spaced proximally from said first opening, said second opening being covered by said covering sheath, said covering sheath having a length equal to or less than the length of the catheter shaft minus the length of the balloon, said covering sheath having guidewire passage means for enabling passage of the guidewire from an interior of the covering sheath to an exterior of the covering sheath, said guidewire being secured between said covering sheath and said shaft, and said catheter shaft having first and second opposite peripheral sides, said balloon being provided on said first peripheral side while said second opening is provided on said second peripheral side.

2. A catheter assembly according to claim 1, further comprising a guiding catheter for inserting said catheter and said covering sheath therethrough.

3. A catheter assembly according to claim 1, wherein said shaft is provided in its periphery with a longitudinal groove to hold the guidewire, said longitudinal groove extending between said second opening of the lumen and a location in the shaft corresponding to the proximal end or a proximal end portion of the covering sheath.

4. A catheter assembly according to claim 1, wherein said guidewire passage means is a longitudinal slit or a thin-walled portion formed in said covering sheath, said slit or said thin-walled portion being provided on at least one end thereof with a guide for guiding the guidewire into said slit or said thin-walled portion.

5. A catheter assembly according to claim 1, including a holder provided on one end of said covering sheath.

6. A catheter assembly according to claim 1, wherein said second opening of the lumen is located proximal to said proximal end of the balloon or distal to said distal end of the balloon.

7. A catheter assembly comprising:

a catheter which comprises:
    a shaft comprised of flexible polymer material, said shaft having a distal end and a proximal end, said shaft possessing a periphery, and
    an inflatable/deflatable balloon provided on the distal end portion of the shaft, said inflatable/deflatable balloon having a distal end and a proximal end;

a covering sheath for covering said catheter together with a guidewire, said covering sheath comprising a synthetic resin material, said covering sheath having a distal end and a proximal end;

said catheter having a lumen extending in said catheter for insertion of the guidewire therethrough, said lumen having a first opening on the distal end of the shaft and a second opening on the periphery of the shaft at a location spaced proximally from said first opening, said second opening being covered by said covering sheath, said covering sheath having a length equal to or less than the length of the catheter shaft minus the length of the balloon, said covering sheath having guidewire passage means for enabling passage of the guidewire from an interior of the covering sheath to an exterior of the covering sheath, said guidewire being secured between said covering sheath and said shaft, and said catheter shaft being made of a flexible polymer material, and said covering sheath being made of a material having a rigidity higher than the catheter shaft.

8. A catheter assembly according to claim 7, further comprising a guiding catheter for inserting said catheter and said covering sheath therethrough.

9. A catheter assembly according to claim 7, wherein said shaft is provided in its periphery with a longitudinal groove to hold the guidewire, said longitudinal groove extending between said second opening of the lumen and a location in the shaft corresponding to the proximal end or a proximal end portion of the covering sheath.

10. A catheter assembly according to claim 7, wherein said guidewire passage means is a longitudinal slit or a thin-walled portion formed in said covering sheath, said slit or said thin-walled portion being provided on at least one end thereof with a guide for guiding the guidewire into said slit or said thin-walled portion.

11. A catheter assembly according to claim 7, including a holder provided on one end of said covering sheath.

12. A catheter assembly according to claim 7, wherein said second opening of the lumen is located proximal to said proximal end of the balloon or distal to said distal end of the balloon.

13. A catheter assembly comprising:

a catheter which comprises:
    a shaft having a distal end and a proximal end, said shaft possessing a periphery, and
    an inflatable/deflatable balloon having a distal end and a proximal end, said inflatable/deflatable balloon being provided on a distal end portion of the shaft;

a covering sheath for covering said catheter together with a guidewire, said covering sheath having a distal end and a proximal end;

said catheter having a lumen extending in said catheter for insertion of the guidewire therethrough, said lumen having a first opening on the distal end of the shaft and a second opening on the periphery of the shaft at a location spaced proximally from said first opening;

said covering sheath having guidewire passage means for enabling passage of said guidewire from an interior of said covering sheath to an exterior of said covering sheath, said guidewire passage means being a slit formed between two overlapping opposite edges of a sheet curled by contraction force; and said guidewire being secured between said covering sheath and said shaft.

14. A catheter assembly according to claim 13, further comprising a guiding catheter for inserting said catheter and said covering sheath therethrough.

15. A catheter assembly according to claim 13, the periphery of said shaft possesses a longitudinal groove to hold the guidewire therein, the longitudinal groove extending between said second opening of the lumen and a location in the shaft corresponding to the proximal end or a proximal end portion of the covering sheath.

16. A catheter assembly according to claim 13, wherein said second opening of the lumen is proximal to said proximal end of the balloon or distal to said distal end of the balloon.

17. A catheter assembly according to claim 13, wherein said catheter shaft has first and second opposite peripheral sides, and said balloon is provided on the first peripheral side while said second opening is provided on the second peripheral side.

18. A catheter assembly according to claim 13, wherein said catheter shaft is made of a flexible polymer material, and said covering sheath is made of a material having a rigidity higher than the catheter shaft.

* * * * *